(12) United States Patent
Pelerin

(10) Patent No.: US 6,395,802 B1
(45) Date of Patent: *May 28, 2002

(54) DENTAL COMPOSITE

(75) Inventor: Joseph J. Pelerin, Clarkston, MI (US)

(73) Assignee: Advantage Dental Products, Inc., Lake Orion, MI (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/283,380

(22) Filed: Mar. 31, 1999

(51) Int. Cl.$^7$ ............................................. A61K 8/063
(52) U.S. Cl. ..................... 523/116; 523/115; 524/533; 433/228.1
(58) Field of Search .................. 523/115, 116; 524/493, 533; 433/228.1

(56) References Cited

U.S. PATENT DOCUMENTS

| | | | |
|---|---|---|---|
| 4,661,536 A | * | 4/1987 | Dorman et al. |
| 4,718,910 A | * | 1/1988 | Draenert |
| 4,721,735 A | | 1/1988 | Bennett et al. ............... 522/71 |
| 4,937,144 A | * | 6/1990 | Podszun et al. |
| 5,251,641 A | | 10/1993 | Xavier ...................... 128/754 |
| 5,318,999 A | | 6/1994 | Mitra et al. .................... 522/57 |
| 5,356,951 A | * | 10/1994 | Yearn |
| 5,472,991 A | | 12/1995 | Schmitt et al. ................. 522/4 |
| 5,723,007 A | | 3/1998 | Engel et al. ................... 623/11 |
| 5,749,733 A | | 5/1998 | Qian et al. ............... 433/228.1 |
| 5,883,153 A | * | 3/1999 | Roberts et al. |

FOREIGN PATENT DOCUMENTS

EP 0499435 A2 8/1992 ........... C08L/69/00

OTHER PUBLICATIONS

Skaguchi, R.L.; Versluis, A.; Douglas, W.H., "Analysis of strain gage method for measurement of post–gel shrinkage in resin composites", Dental Materials 13, (4) 1997; Jul. 1997 pp. 233–239.

McCabe, J.F.; Rusby, S., "Dentine bonding—the effect of pre–curing the bonding resin", Br Dent J, vol. 176, No. 9, 1994 May 7, pp. 333–336.

Bradburn, G.; Pender, N., "An in vitro study of the bond strength of two light–cured composites used in the direct bonding of orthodontic to molars", Am J Orthod Dentofacial Orthop, vol. 102, No. 5, 1992 Nov., pp. 418–426.

Fellman, S., "Visible light–cured denture base resin used in making denstures with conventional teeth", J of Prosthet Dent, vol. 62, No. 3, 1989 Sep., pp. 356–359.

* cited by examiner

Primary Examiner—Peter Szekely
(74) Attorney, Agent, or Firm—Gifford, Krass, Groh, Sprinkle, Anderson & Citkowski, P.C.

(57) ABSTRACT

A dental composite is disclosed which is made of a light curable material containing filler particles suspended in the light curable material. The filler particles are formed from material that has been previously cured and then reduced in size, preferably by grinding, to a predetermined range of particle sizes.

6 Claims, 1 Drawing Sheet

DENTAL COMPOSITE

Background of the Invention

I. Field of the Invention

The present invention relates generally to dental products and, more particularly, to a dental composite.

II. Description of the Prior Art

In modern day dentistry, following a cavity preparation, the use of dental composites to fill the cavity preparation in lieu of amalgam has enjoyed widespread acceptance. One reason for this widespread acceptance is that the composite, because it is light colored, is cosmetically more pleasing than amalgam or gold fillings.

In filling a cavity preparation with a dental composite, the cavity preparation is first sterilized and the dental composite in an uncured state is applied and driven into the cavity preparation. In an uncured state, the dental composite typically has a paste-like consistency.

After the dental composite has filled the cavity preparation, the dental composite is light cured, which causes the dental composite to harden and adhere to the tooth. After the dental composite has cured, the dental composite is polished or otherwise shaped to conform to the tooth.

The previously known dental composites, however, have suffered from a number of disadvantages. One disadvantage is that the composite material, due to its paste-like consistency, tends to squish out of the cavity preparation when the dentist drives the composite into the cavity preparation. This, in turn, requires that the dentist apply additional composite and again refill the cavity preparation.

A still further disadvantage of these previously known dental composites is that the dental composite shrinks somewhat during curing. This shrinkage may result in an unsatisfactory bond between the tooth and the dental composite and/or unsatisfactory appearance.

Lastly, the previously known dental composites require relatively lengthy light curing which adds to the overall length of the dental procedure. This in turn results in decreased productivity for the dentist.

SUMMARY OF THE PRESENT INVENTION

The present invention provides a dental composite which overcomes the above-mentioned disadvantages of the previously known dental composites.

In brief, the dental composite of the present invention is formed from a light curable material which contains filler particles suspended within the material. Typically, the light curable material has a paste-like consistency and a particle size in the range of 1 to 15 microns. Conversely, the filler particles are preferably in a range of 5 microns to 4 millimeters in size.

The filler particles are formed from the same light curable material as the composite that has been cured and then ground in order to obtain the desired particle size and optionally, contain filler particles of different material. Consequently, when the filler particles are intermixed with the paste, applied to a cavity preparation and then cured, the resulting cured composite enjoys a homogenous structure.

The present invention, by utilizing filler particles formed of the same material as the uncured dental composite material, effectively increases the viscosity of the dental composite and thus enjoys improved drivability during the filling of a cavity preparation.

A still further advantage of the dental composite of the present invention is that the filler particles will not further shrink during a light cure of the dental composite. As such, the dental composite of the uncured material with the suspended particles exhibits less shrinkage during cure than the previously known dental composites.

A still further advantage of the dental composite of the present invention is that the dental composite will be cured in less time than the previously known dental composites. This faster cure of the present invention is achieved since the filler particles have already been cured prior to the application of the dental composite to the cavity preparation thereby resulting in reduced curing time.

Still further advantages of the present invention will become apparent to those skilled in the art.

A method for making the dental composite is also disclosed.

BRIEF DESCRIPTION OF THE DRAWING

A better understanding of the present invention will be had upon reference to the following detailed description when read in conjunction with the accompanying drawing, wherein like reference characters refer to like parts throughout the several views, and in which.

DETAILED DESCRIPTION OF A PREFERRED EMBODIMENT OF THE PRESENT INVENTION

Figure 1:
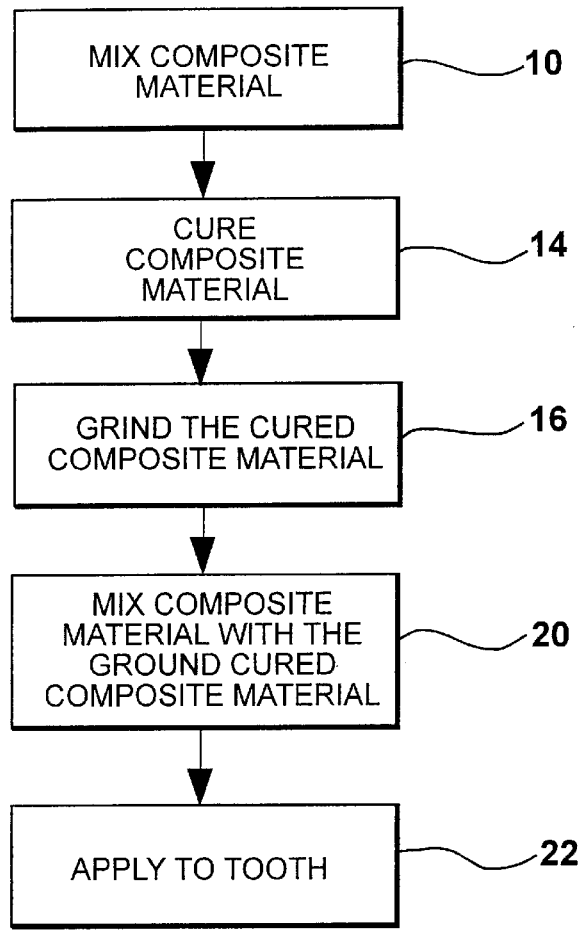
FIG. 1 is a process diagram illustrating the method of making the dental composite of the present invention.

With reference first to FIG. 1, in order to make the dental composites of the present invention, a light curable material 10 is first completely cured by exposing the material 10 to an appropriate light source as shown at step 14. Optionally, the material 10 is cured under pressure, heat or other special conditions. Following curing of the material 10, the material 10 is hardened. Furthermore, the material 10 may be any conventional dental composite material.

At step 16, the hardened material 10 is reduced in size, preferably by grinding, to particles within a preset range. Preferably, this preset range is between 5 microns and 4 millimeters in size. These particles then form filler particles 18.

At step 20, the filler particles 18 are intermixed with uncured light curable material 10 such that the filler particles 18 are suspended as uniformly as possible within the uncured dental composite material 10. The intermixing of the filler particles 18 into the uncured material 10 increases the overall viscosity of the material 10. The amount of filler material intermixed with the uncured material ranges from 5 to 95% by weight of the resulting mixture.

Figure 2:
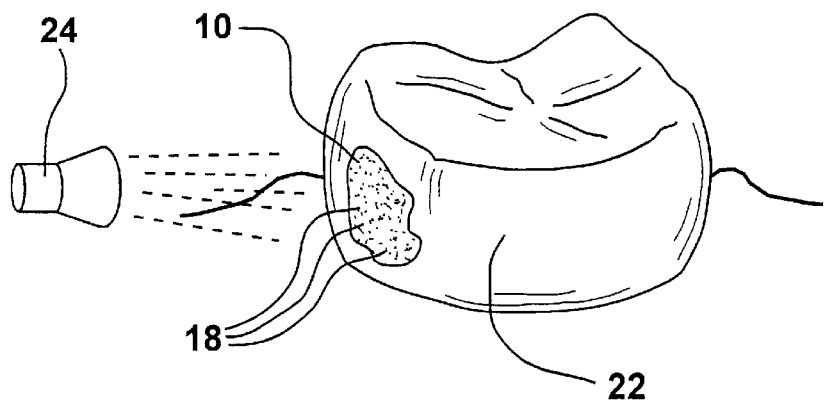
FIG. 2 is a diagrammatic view illustrating the use of the dental composite of the present invention.

As shown at step 22 and also in FIG. 2, after the filler, particles 18 have been intermixed into the uncured material 10, the resulting dental composite is applied to a cavity preparation in a tooth 22. The dental composite, i.e. the uncured material with the suspended filler particles, is then cured by using a conventional curing light 24. After curing, the dental composite is shaped by polishing in order to complete the dental procedure.

A primary advantage of the dental composite of the present invention is that, since the filler particles effectively increase the Viscosity of the uncured dental composite material, the dental composite of the present invention enjoys improved drivability with respect to uncured dental composite material without the filler.

A still further advantage of the dental composite of the present invention is that the filler particles will not further shrink as the overall dental composite material is cured. This, in turn, results in less shrinkage of the overall dental composite material, i.e. the uncured material with the suspended filler particles, as opposed to uncured material without the filler. Furthermore, since the dental composite of the present invention includes filler particles that have already been cured, the overall curing time for the dental composite of the present invention is reduced thus reducing the overall time required for the procedure.

Further, the filler particles reduce or eliminate air voids and facilitate packing of the composite into a preparation. The composite of the present invention also provides improved polishing surface texture since the light curable material and filler particles are the same material having 1 to 15 micron size.

Having described my invention, however, many modifications thereto will become apparent to those skilled in the art to which it pertains without deviation from the spirit of the invention as defined by the scope of the appended claims.

I claim:

1. A dental composite comprising:

a light curing material; and a filler wherein said filler consists of: ground cured filler particles of light curing material suspended in said light curing material resulting in a homogeneous composition upon light cure.

2. The invention as defined in claim 1 wherein said filler particles are formed by grinding said material that has been cured to a selected range of particle sizes.

3. The invention as defined in claim 2 wherein said particles range in size from 5 microns to 4 millimeters.

4. The invention as defined in claim 1 wherein said filler particles range from five to 95% by weight of the composite.

5. An improved dental composition containing a curing material and a particulate filler wherein the improvement lies in: said curing material being light curing and said filler consisting of said curing material resulting in a homogenous composition upon light cure.

6. A dental composite consisting essentially of:

a light curing material; and a filler wherein said filler consists of: ground cured filler particles of light curing material suspended in said light curing material.

* * * * *